(12) United States Patent
Vuillerme et al.

(10) Patent No.: US 8,454,539 B2
(45) Date of Patent: Jun. 4, 2013

(54) METHOD AND DEVICE FOR DETECTING AND PREVENTING PLANTAR ULCERS

(75) Inventors: Nicolas Vuillerme, Francin (FR); Norbert Noury, Grenoble (FR); Yohan Payan, Allevard (FR); Jacques Demongeot, Sassenage (FR)

(73) Assignee: Universite Joseph Fourier, Grenoble Cedex (FR)

( * ) Notice: Subject to any disclaimer, the term of this patent is extended or adjusted under 35 U.S.C. 154(b) by 629 days.

(21) Appl. No.: 12/304,062

(22) PCT Filed: Jun. 8, 2007

(86) PCT No.: PCT/FR2007/051399
§ 371 (c)(1),
(2), (4) Date: Apr. 21, 2010

(87) PCT Pub. No.: WO2008/006995
PCT Pub. Date: Jan. 17, 2008

(65) Prior Publication Data
US 2010/0198022 A1    Aug. 5, 2010

(30) Foreign Application Priority Data

Jun. 9, 2006   (FR) ...................................... 06 52073

(51) Int. Cl.
*A61B 5/01*    (2006.01)
*A61B 5/00*    (2006.01)
*G08B 23/00*   (2006.01)

(52) U.S. Cl.
USPC ............................. 600/592; 600/549; 600/301

(58) Field of Classification Search
USPC ............ 600/300, 344, 587, 301, 592; 607/48, 607/58; 36/136
See application file for complete search history.

(56) References Cited

U.S. PATENT DOCUMENTS

| | | | | |
|---|---|---|---|---|
| 5,237,501 A | * | 8/1993 | Gusakov | 600/587 |
| 5,578,066 A | * | 11/1996 | Gober | 607/58 |
| 5,642,096 A | * | 6/1997 | Leyerer et al. | 340/573.1 |
| 5,929,332 A | * | 7/1999 | Brown | 73/172 |

(Continued)

FOREIGN PATENT DOCUMENTS

| | | |
|---|---|---|
| DE | 4308945 A1 | 11/1993 |
| JP | 2001238967 | 9/2001 |
| WO | 03079882 A2 | 10/2003 |
| WO | 03079882 A3 | 10/2003 |

OTHER PUBLICATIONS

Patel et al., Temperature Effects on Surface Pressure-Induced Changes in Rat Skin Perfusion: Implications in Pressure Ulcer Development, 36 Journal of Rehabilitation Research & Development. 3(1999). (Accessed Oct. 25, 2011. Note: Found at http://www.rehab. research.va.gov/jour/99/36/3/patel.htm, look at entire article and Introduction).*

(Continued)

*Primary Examiner* — Sean P Dougherty
*Assistant Examiner* — Michael C Stout
(74) *Attorney, Agent, or Firm* — Howard IP Law Group, P.C.

(57) ABSTRACT

A method of detecting a risk of occurrence of a plantar ulcer includes the following steps: monitoring at least the temperature and pressure of the sole of at least one foot; as soon as one of the temperature and pressure parameters exceeds a threshold value, opening a first time window for monitoring the first parameter; if at the end of the first time window the first parameter still exceeds the threshold value, monitoring the second parameter during a second time window; and assigning a coefficient of risk to the event encountered.

8 Claims, 1 Drawing Sheet

U.S. PATENT DOCUMENTS

| | | | |
|---|---|---|---|
| 6,195,921 B1 * | 3/2001 | Truong | 36/136 |
| 6,366,815 B1 * | 4/2002 | Haugland et al. | 607/48 |
| 6,398,740 B1 * | 6/2002 | Lavery et al. | 600/549 |
| 7,771,371 B2 * | 8/2010 | Avni | 600/592 |
| 2004/0199063 A1 * | 10/2004 | O'Neil et al. | 600/344 |
| 2005/0165284 A1 * | 7/2005 | Gefen | 600/300 |

OTHER PUBLICATIONS

Caselli et al. "The Forefoot-to-Rearfoot Plantar Pressure Ratio Is Increased in Severe Diabetic Neuropathy and Can Predict Foot Ulceration" Diabetes Care, vol. 25, No. 6, Jun. 2002.*

International Search Report dated Dec. 21, 2007.

* cited by examiner

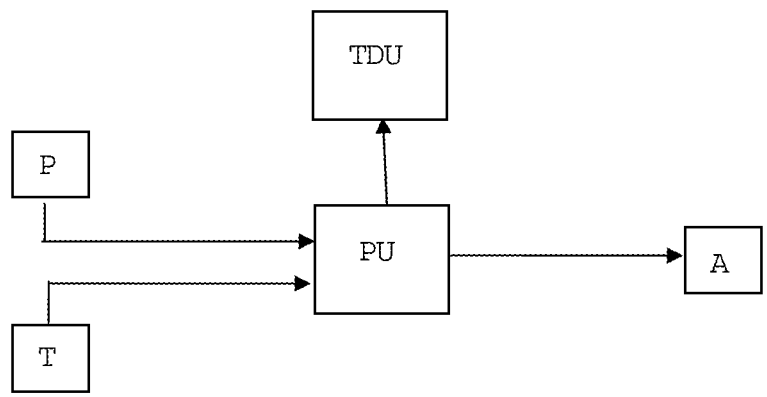

METHOD AND DEVICE FOR DETECTING AND PREVENTING PLANTAR ULCERS

This application is the national stage application under 35 U.S.C. §371 of International Application No. PCT/FR2007/051399 and claims the benefit of Int'l. Application No. PCT/FR2007/051399, filed Jun. 8, 2007 and French Application No. 06/52073, filed Jun. 9, 2006, the entire disclosures of which are incorporated herein by reference in their entireties.

FIELD OF THE INVENTION

The present invention relates to a device for preventing plantar ulcers.

DISCUSSION OF PRIOR ART

Plantar ulcers are becoming a non-negligible public health issue. In particular, an increase in plantar ulcers proportional to the increase of overweight or obese persons can be observed. Further, independently from their excess weight, persons affected with chronic pathologies affecting the circulation, for example, diabetics, are also likely to suffer from plantar ulcers. The formation of plantar ulcers can also be observed after a trauma and/or a surgical operation affecting one of the lower limbs. Indeed, after a trauma or an operation, a person may find it difficult to use the traumatized or operated limb normally and may take a bad position likely to cause ulcers. Further, after a trauma or an operation, a person may be psychologically reluctant to normally letting his weight bear on the traumatized or operated side, which favors the formation of plantar ulcers on the foot located on the non-traumatized or non-operated side.

The formation of plantar ulcers is irreversible. Further, ulcers are difficult, or even impossible to cure and frequently result in a reduction of the mobility of the affected person, or even in an amputation of the affected foot. Such effects have a serious impact on the affected person, physically as well as psychologically.

It has been suggested to "adapt" the gait and the posture of populations at risk to decrease the probability of formation of ulcers. Such an "adaptation" essentially goes through a walk training adapted to the person's risk, in a gymnasium. However, such a training is not definitive and imposes a refreshment and a frequent control. This constraint is all the greater as adapted gymnasiums are often concentrated in large agglomerations and incorporated in hospital centers. Besides the constraints imposed to the person to be trained, this is often also a constraint for the concerned establishments due to the required material and personnel and this, all the more as the follow-up of such persons who do not strictly speaking request medical care is not part of their normal duties.

Further, such a training is seldom personalized and is based on essentially statistical studies. There exists no process or device for detecting risks of formation of plantar ulcers for a given person. The training may then end up being partly inefficient.

The present invention aims at providing a method and a device for detecting the risk of formation of plantar ulcers.

The present invention aims at providing such a device which is simple and likely to be used by a single person without any supervision and any installation.

The present invention also aims at providing an ulcer prevention device enabling to automatically compensate for a risk of plantar ulcer.

SUMMARY OF THE INVENTION

To achieve these and other objects, the present invention provides a method for detecting a risk of formation of a plantar ulcer, comprising the steps of:

monitoring at least the temperature and the pressure of at least one plantar sole;

as soon as a first one of the parameters, temperature or pressure, exceeds a threshold value, opening a first time window for monitoring the first parameter;

if, at the end of the first time window, the first parameter still exceeds the threshold value, monitoring during a second time window the second parameter; and assigning a risk coefficient to the encountered event.

According to an embodiment of the present invention, the blood oxygen level is monitored as a parameter additional to temperature and pressure.

The present invention also provides a method for preventing plantar ulcers, comprising the steps of detecting a risk of formation of a plantar ulcer by means of a method according to one of the previous embodiments, and of delivering a signal to at least one actuator.

According to an embodiment of the present invention, an actuator is capable of delivering a warning signal to the person at risk.

According to an embodiment of the present invention, an actuator is capable of delivering a warning signal to the person at risk.

The present invention also provides a device for detecting a risk of formation of a plantar ulcer, characterized in that it comprises:

a first array of sensors of the temperature of at least one foot sole;

a second array of sensors of the sole pressure;

counters; and a processing unit capable of detecting any exceeding of threshold values by the temperature or the pressure provided by any of the sensors, of starting a first counter as soon as a first one of the temperature or pressure parameters has exceeded the threshold value, of starting a second counter for monitoring the second one of the pressure or temperature parameters if the exceeding of the first parameter is maintained for a first duration set by the first counter, and of calculating a risk coefficient when the second counter has finished counting for a second duration.

According to an embodiment of the present invention, the device further comprises an array of sensors for measuring the blood oxygen level at various points of the plantar sole, the processing unit being capable of processing the blood oxygen level measurements as a parameter additional to the temperature and the pressure.

According to an embodiment of the present invention, the device comprises an actuator capable of delivering to the user of the device a plantar ulcer risk warning signal.

According to an embodiment of the present invention, the actuator capable of delivering a warning signal to the user of the device is a device of electrical stimulation of the tongue.

The present invention also provides a device for preventing plantar ulcers, characterized in that it comprises a device for detecting plantar ulcers according to any of the foregoing embodiments, and at least one actuator capable of causing a reflex movement capable of compensating for the risk of plantar ulcer.

According to an embodiment of the present invention, an actuator capable of causing a reflex movement is an electromyographic actuator.

BRIEF DESCRIPTION OF THE DRAWINGS

The foregoing objects, features, and advantages of the present invention, as well as others, will be discussed in detail in the following non-limiting description of specific embodiments in connection with the FIGURE which schematically illustrates a plantar ulcer prevention device.

DETAILED DESCRIPTION

According to an embodiment of the present invention, the shoe of a person belonging to a population at risk for the formation of plantar ulcers is equipped with various sensors.

In particular, the shoe comprises an array or sheet P of pressure sensors having the shape of the foot and capable of detecting the pressure of the plantar sole. Preferably, array P has an increased density of sensors in the most exposed locations, namely the metatarsal heads, in particular the first and fifth ones, as well as at the heel level.

The shoe also comprises an array T of temperature sensors for measuring the temperature at various points of the plantar sole. Preferably, the number of temperature sensors is larger at locations where the probability of formation of an ulcer is the highest.

The data from sensors P and T are transmitted to a processing unit PU. Unit PU then detects the occurrence of an overpressure or of too high a temperature. For example, unit PU individually compares the temperature data sampled in different areas with threshold values. The threshold values depend on the area associated with the considered sensor. If unit PU detects that a threshold has been exceeded in at least one of these areas, it triggers a counter of a first duration for this area.

If, before the end of the first duration, the excessive temperature state disappears, unit PU does not take this information into account.

If, at the end of the first duration, the excessive temperature state is maintained, unit PU stores this event, that is, the area and the excessive temperature degree. Further, unit PU causes a detection of a possible overpressure by comparing for a second duration the pressure data originating from the area having an excessive temperature with at least one threshold.

If the excessive temperature disappears during the second duration and no overpressure is detected, unit PU just stores the location and duration data. The memory of this event is kept for a third duration. If no other excessive temperature event affects the considered area in the third duration, the event is forgotten.

If, during the second duration, the excessive temperature is maintained, unit PU assigns to this area an ulcer risk coefficient. This coefficient is modulated according to the occurrence of an overpressure. The coefficient is higher when a pressure higher than normal has been detected, in the second duration.

Once the second duration has elapsed, unit PU takes into account the history stored for the concerned area and modifies, if necessary, the risk coefficient according to the past events which have occurred during a past time window corresponding to the third duration and ending at the end of the second duration.

The risk coefficient is then compared with at least one prevention threshold.

Once the prevention threshold has been exceeded, unit PU sends according to an embodiment of the present invention a warning signal to the person.

According to an embodiment of the present invention, the signal is sent to a tongue display unit TDU. Such a TDU is generally formed at least of an artificial palate capable of being placed in the oral cavity and supporting an array of electrodes likely to enter into contact at least with the upper surface of the tongue. The signal then exhibits a coding capable of activating predefined areas of the electrode array. The coding enables to indicate to the person either the location and the degree of the risk, or an action to be taken to decrease the risk of formation of a plantar ulcer. The coding mode is selected according to the affected person and to his or her capacity of analyzing the situation.

According to another embodiment of the present invention, whether or not the information on the risk of formation of the ulcer is transmitted to the user, unit PU is capable of triggering actuators A placed in the shoe and capable of suppressing the risk of ulcer.

Such actuators A for example are electromyographic actuators placed under the plantar sole at the level of the muscles governing the ankle and which cause a contraction stimulation of a tendon, of a tactile receiver, or of a muscle, corresponding to the area at risk. This stimulation is unconsciously felt by the person as a real movement of his own body and leads him to displace, as a reflex, the area capable of compensating for this movement, thus causing a displacement capable of suppressing the risk.

Another type of actuators A is an actuator capable of performing a mechanical stimulation. This stimulation may be felt, like the previous electromyographic stimulation, as a displacement of the foot and cause a reflex displacement of the foot capable of compensating for the risk of ulcers. Further, a mechanical stimulation is similar to a massage and causes micro-displacements which relieve the affected area.

It should be noted that the actuators may also be placed, rather than under the feet, on other parts of the body, especially the lower limbs to cause a posture modification. Indeed, a plantar ulcer may also result, for example, from a bad position of the leg.

A device and a method for detecting risks of plantar ulcers have thus been provided.

Further, as completed by the actuators, the device enables preventing the forming of ulcers.

The method and the device according to the present invention have many advantages.

In particular, they enable to dispense the person from going to specialized gymnasiums or to decrease the frequency of the visits. This suppresses the associated constraints, for the person as well as for the establishment.

Further, the device is embarked and inconspicuous: the soles supporting the appropriate sensors and actuators may be designed to fit in a shoe, the PU is a box of small size which can be placed in a pocket or attached to a belt. Preferably, the device is designed with a technology of wireless communication between processing unit PU and sensors T and P and between processing unit PU and actuators TDU and A.

Of course, the present invention is likely to have different variations and modifications which will occur to those skilled in the art. In particular, an embodiment in which the detection of the risk of ulcers is based on a first detection of an excessive temperature which causes the opening of a time window during which unit PU detects the occurrence of a possible overpressure has been described. However, it would also be possible to perform a first detection of an overpressure, then to cause the opening of a time window during which unit PU detects the occurrence of an excessive temperature.

Preferably, according to an embodiment of the present invention, unit PU permanently monitors the temperature and the pressure and is likely to cause, as soon as one of these two parameters has exceeded a threshold value, the opening of a time window during which it detects the occurrence of a possible excessive value of the other parameter.

It should be noted that the triggering thresholds of the counters and the monitoring durations vary according to the concerned area. Thus, in a normal walk, the heel supports for a short time a significant weight and abruptly warms up in corresponding manner for a short time corresponding to the first bearing of a lifted foot. Similarly, when a foot is being lifted, the weight is momentarily totally supported by the metatarsal heads. The excessive pressure level further differs according to the considered area. Thus, a level considered as normal in the heel area will be considered as excessive in a metatarsal head area. The threshold levels programmed in the processing unit depend on the individual's weight, size, and morphology.

According to an embodiment of the present invention, the risk coefficient is modulated according to the value by which the temperature and the pressure have been exceeded with respect to normal values. Thus, for a same excessive temperature, the coefficient will be lower in the case where the pressure has only exceeded normal values towards the end of the second duration than in the case where the pressure was already greater than normal at the beginning of the second duration.

Further, in the previously-described embodiments, only the temperature and the pressure have been taken into account. It should however be noted that other parameters may be taken into account. In particular, for a person with a high risk of ulcer formation, one or several sensors for detecting the blood oxygen level may be used. Such a parameter is used to accelerate the detection of a risk. Indeed, if too high a pressure and/or a temperature are detected in a given area, the risk of ulcer is all the higher as the blood oxygen level is low.

The invention claimed is:

1. A method for detecting a risk of formation of a plantar ulcer, comprising the steps of:
   monitoring, in a processing unit, a temperature parameter indicative of a temperature of at least one plantar sole;
   monitoring, in the processing unit, a pressure parameter indicative of a pressure of at least one plantar sole;
   in response to a first one of the temperature and the pressure parameters, exceeding a threshold value in an area of the plantar sole defining an event, causing the processing unit to open a first time window for monitoring the first parameter that exceeded the threshold value;
   if, at the end of the first time window, the first parameter still exceeds the threshold value, monitoring during a second time window the other one of the parameters in the area of the plantar sole; and
   assigning a risk coefficient to the event in said area of the sole and sending a warning signal if the risk coefficient exceeds a prevention parameter.

2. The method of claim 1, wherein an oxygen parameter indicative of a blood oxygen level is also monitored.

3. A device for detecting a risk of formation of a plantar ulcer, comprising:
   a first array of sensors for sensing a temperature of a foot sole;
   a second array of sensors for sensing a pressure of the foot sole;
   a plurality of counters; and
   a processing unit adapted to:
      detect any exceeding of one of a plurality of threshold values by a temperature or a pressure provided by any of the sensors,
      start a first of said plurality of counters when a first of the temperature or pressure provided by any of the sensors has exceeded the one of the plurality of threshold values,
      start a second of said plurality of counters for monitoring the second one of the pressure or temperature parameters if the exceeding of the one of the plurality of threshold values by the first parameter is maintained for a first duration set by the first counter, and
      calculate a risk coefficient when the second counter has finished counting for a second duration and sending a warning signal if the risk coefficient exceeds a prevention threshold.

4. The device of claim 3, further comprising a third array of sensors for measuring a blood oxygen level at a plurality of points of the plantar sole, wherein the processing unit is adapted to process the blood oxygen level measurements as an oxygen parameter additional to the temperature and the pressure.

5. The device of claim 3, further comprising an actuator adapted to deliver to a user of the device a plantar ulcer risk warning signal.

6. The device of claim 5, wherein the actuator comprises a device providing an electrical stimulation of the tongue of the user.

7. A device for detecting a risk of and preventing plantar ulcers, comprising:
   a first array of sensors for sensing a temperature of at a foot sole;
   a second array of sensors for sensing a pressure of the foot sole;
   a plurality of counters; and
   a processing unit adapted to:
      detect any exceeding of one of a plurality of threshold values by a temperature value or a pressure value provided by any of the sensors,
      start a first of said plurality of counters when a first of the temperature value or pressure value provided by any of the sensors has exceeded the one of the plurality of threshold values,
      start a second of said plurality of counters for monitoring the second one of the pressure value or temperature value if the exceeding of the one of the plurality of threshold values by the first parameter is maintained for a first duration set by the first counter, and
      calculate a risk coefficient when the second counter has finished counting for a second duration; and
   at least one actuator adapted to cause a reflex movement capable of decreasing the risk of plantar ulcer in response to a trigger signal from the processing unit.

8. The device of claim 7, wherein the at least one actuator is an electromyographic actuator.

* * * * *